United States Patent [19]
Greenwald et al.

[11] Patent Number: 5,824,701
[45] Date of Patent: *Oct. 20, 1998

[54] TAXANE-BASED PRODRUGS

[75] Inventors: Richard B. Greenwald, Somerset; Annapurna Pendri, Matawan, both of N.J.

[73] Assignee: Enzon, Inc., Piscataway, N.J.

[*] Notice: The term of this patent shall not extend beyond the expiration date of Pat. No. 5,622,986.

[21] Appl. No.: 794,730

[22] Filed: Feb. 3, 1997

Related U.S. Application Data

[63] Continuation-in-part of Ser. No. 351,462, Dec. 12, 1994, Pat. No. 5,622,986, which is a continuation-in-part of Ser. No. 140,346, Oct. 20, 1993, abandoned.

[51] Int. Cl.⁶ ........................ A61K 31/335; C07D 305/14
[52] U.S. Cl. ........................ 514/449; 549/510; 549/511; 528/421
[58] Field of Search ............................ 514/449; 549/510, 549/511; 528/421

[56] References Cited

U.S. PATENT DOCUMENTS

| | | | |
|---|---|---|---|
| 5,284,865 | 2/1994 | Holton et al. | 514/449 |
| 5,411,984 | 5/1995 | Kingston et al. | 214/449 |
| 5,422,364 | 6/1995 | Nicolaou et al. | 514/449 |
| 5,489,589 | 2/1996 | Wittman et al. | 514/232.8 |
| 5,530,020 | 6/1996 | Gunawardana et al. | 514/449 |

(List continued on next page.)

OTHER PUBLICATIONS

Georg, G. et al., "Synthesis and Biology of Substituted 3'–Phenyl Taxol Analogues",*Bioorganic and Med. C Letters*, vol. 4, No. 19; pp. 2231–2236, (1994).

(List continued on next page.)

*Primary Examiner*—Ba K. Trinh
*Attorney, Agent, or Firm*—Roberts & Mercanti, LLP

[57] ABSTRACT

Taxane-based compositions of the formula

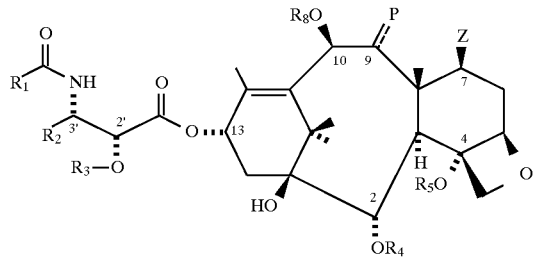

wherein
$R_1$ is selected from the group consisting of aryls, substituted aryls, aralkyls, substituted aralkyls, alkyls and substituted alkyls;

$R_2$ is an aryl or substituted aryl, preferably phenyl;
$R_3$ is H, a $C_{1-10}$ alkoxy, $SiEt_3$ or

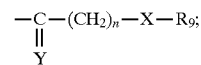

Y is O or S;
(n) is zero or a positive integer;
X is oxygen, S, $SO_2$ or NL, where L is selected from the group consisting of H, $C_{1-8}$ alkyls, aryls and aralkyls;
$R_4$ is H or an aroyl of the formula:

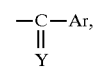

wherein Ar is an aromatic, substituted aromatic or heteroaromatic group;

$R_5$ is H, $CH_3CO$ or a substituted acetic acid derivative;
Z is H or $OR_6$ where $R_6$ is selected from the group consisting of H, $C_{1-8}$ alkyls, $C_{1-8}$ substituted alkyls, $C_{1-8}$ aralkyls, substituted aryls, aralkyls, substituted aralkyls, $C_{1-10}$ alkoxy, $SiEt_3$,

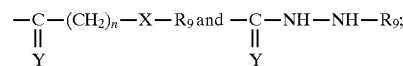

P is O or OH;
$R_8$ is one of H, $S(CH_3)_3$, $Si(C_2H_5)_3$, $CH_3CO$, or substituted acetic acid derivatives of the formula;

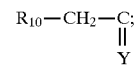

where
$R_{10}$ is an alkyl, aryl, halogen, or hydrogen alkoxy or

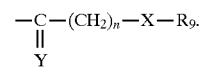

$R_9$ is selected from the group consisting of substantially non-antigenic polymers, $C_{1-12}$ alkyls, $C_{1-12}$ substituted alkyls and bifunctional moieties such as alkyls or polymers containing a terminal group

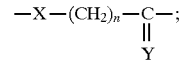

and one of $R_3$, $R_6$ and $R_8$ is

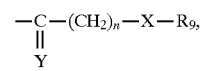

and methods of preparation and use of the compounds are also disclosed.

28 Claims, 5 Drawing Sheets

U.S. PATENT DOCUMENTS

| | | | |
|---|---|---|---|
| 5,547,981 | 8/1996 | Greenwald et al. | 514/449 |
| 5,622,986 | 4/1997 | Greenwald et al. | 514/449 |
| 5,681,964 | 10/1997 | Ashton et al. | 548/491 |

OTHER PUBLICATIONS

Georg, G. et al., "Selective C–2 and C–4 Deacylation and Acylation of Taxol: The First Synthesis of a C–4, Substituted Taxol Analogue", *Tetrahedron Letters*, vol. 35, No. 48; pp. 8931–8934, (1994).

Ueda Y. et al., "Synthesis and Antitumor Evaluation of 2'–Oxycarbonylpaclitaxels (Paclitaxel–2'–Carbonates)", *Bioorganic and Med. Chem. Letters*; vol. 4, No. 15; pp. 1861–1864, (1994).

Ueda Y. et al., "Novel, Water–Soluble Phosphate Derivaties of 2'–Ethoxy Carbonylpaclitaxel as Potential Prodrugs of Paclitaxel: Syntheses and Antitumor Evaluation",*Bioorg.& Med. Chem. Ltrs*; vol. 5 No. 3: pp. 247–252; (1995).

6: $R_3 = H$
7: $R_3 = PEG_{40k}-O-CH_2-CO$

TAXANE-BASED PRODRUGS

CROSS-REFERENCE TO RELATED APPLICATIONS

This application is a continuation-in-part of U.S. patent application Ser. No. 08/351,462 filed Dec. 12, 1994 now U.S. Pat. No. 5,622,986, which, in turn is a continuation-in-part of U.S. patent application Ser. No. 08/140,346 filed Oct. 20, 1993, now abandoned. The contents of each of the foregoing applications are incorporated herein by reference.

TECHNICAL FIELD

The present invention relates to prodrug compounds having anti-microtubule activity. In particular, the invention relates to polymer-based taxane prodrugs which demonstrate enhanced anti-neoplastic activity and/or improved water-solubility.

BACKGROUND OF THE INVENTION

Paclitaxel (taxol) is relatively new anti-cancer agent. Paclitaxel is a plant product derived in minute quantities from the needles and bark of the western pacific yew, *Taxus brevifolia*. In chemotherapy, paclitaxel is known as an anti-microtubule agent and is thought to inhibit cell mitosis through the enhancement of the rate of microtubular assembly and prevention of microtubular depolymerization. Numerous studies indicate that the agent has activity against several malignancies. To date, its use has been severely limited by, among other things, it short supply, poor water solubility and immunogenicity.

The pacific yew is a rare, slow-growing tree which is not typically cultivated. In addition, the anti-neoplastic portions of the tree are very minute. Extraction of these portions is complicated and costly. One solution to the problem of short supply has been suggested in U.S. Pat. No. 5,019,504 which discloses an artificial media for producing certain desirable alkaloids. Alternatively, synthetic derivations such as taxotere and paclitaxel intermediates have also been reported. See, for example, U.S. Pat. No. 5,015,744.

Hypersensitivity reactions from paclitaxel administration are known. See, for example, *J. Clin. Oncol.* 8:1263–1268 (1990). Indeed, since taxoids are usually extracted from a natural plant source, some hypersensitivity is expected. Moreover, certain non-queous vehicles which have been used to overcome the water solubility problems of paclitaxel have also been implicated in causing hypersensitivity reactions.

Although paclitaxel and related compounds hold promise as therapeutic agents, there is a need to provide taxoid-based derivatives which are more water soluble and/or are more active against a wider range of neoplasms than paclitaxel.

SUMMARY OF THE INVENTION

In one aspect, the present invention is generally directed to taxanes which have been modified in one or more of the side chain, i.e. the 2'- or 3' positions and/or one of the 2-, 4-, 7-, 9- and/or 10- positions. The numbering of the taxane structure is based upon the commonly accepted numbering system used to identify paclitaxel. The modifications are preferably designed to provide prodrug-taxanes, taxols, substituted taxanes or substituted taxols. Additional aspects of the invention include methods of preparing the compositions and their use in mammals.

The inventive compositions thus include compositions of the formula: (I)

wherein:

$R_1$ is selected from the group consisting of aryls, substituted aryls, aralkyls, substituted aralkyls, alkyls and substituted alkyls;

$R_2$ is an aryl or substituted aryl, preferably phenyl;

$R_3$ is H, a $C_{1-10}$ alkoxy, such as $OCH_3$, $OCH_2CH_3$, etc., $SiEt_3$ or $$-\underset{\underset{Y}{\|}}{C}-(CH_2)_n-X-R_9;$$

Y is O or S;

(n) is zero or a positive integer;

X is oxygen, S, $SO_2$ or NL, where L is selected from the group consisting of H, $C_{1-8}$ alkyls, aryls and aralkyls;

$R_4$ is H or an aroyl of the formula $$-\underset{\underset{Y}{\|}}{C}-Ar,$$

where Ar is an aromatic, substituted aromatic or heteroaromatic group;

$R_5$ is H, $CH_3CO$ or a substituted acetic acid derivative;

Z is H or $OR_6$ is selected from among H, $C_{1-8}$ alkyls, $C_{1-8}$ substituted alkyls, $C_{1-8}$ aralkyls, substituted aryls, aralkyls, substituted aralkyls, $C_{1-10}$ alkoxys, $SiEt_3$, $$-\underset{\underset{Y}{\|}}{C}-(CH_2)_n-X-R_9 \text{ and } -\underset{\underset{Y}{\|}}{C}-NH-NH-R_9;$$

P is O or OH;

$R_8$ is one of H, $S(CH_3)_3$, $Si(C_2H_5)_3$, $CH_3CO$, or substituted acetic acid derivatives of the formula;

$$R_{10}-CH_2-\underset{\underset{Y}{\|}}{C};$$

where $R_{10}$ is an alkyl, aryl halogen, or hydrogen alkoxy or $$-\underset{\underset{Y}{\|}}{C}-(CH_2)_n-X-R_9.$$

$R_9$ is selected from the group consisting of substantially non-antigenic polymers, $C_{1-12}$ alkyls, $C_{1-12}$ substituted alkyls and bifunctional moieties such as alkyls or polymers containing a terminal group $$-X-(CH_2)_n-\underset{\underset{Y}{\|}}{C}-;$$

and one or $R_3$, $R_6$ and $R_8$ is

Another particularly preferred aspect of the invention provides PEG-based ester-linked prodrugs, i.e. where (n) is one and $R_9$ includes a polyethylene glycol having a molecular weight of from about 200 to about 80,000. Within this embodiment, the polymeric ester is preferably attached in the 2'-position of the taxane or substituted taxanes as defined herein.

The invention includes inter alia the following types of taxoid-based compositions:

i) 7-carbonates; 2'-carbonates;

ii) 7-polymeric esters; 2'-polymeric esters;

iii) 2'-polymeric ester-7-carbonates;

iv) 2',7-disubstituted polymeric esters; 2',7-disubstituted carbonates; and v) combinations thereof.

In alternative aspects, the invention also includes taxanes or substituted taxanes which have been modified in one or more of the 2-, 4-, 9- and 10- positions. A high molecular weight polymeric ester can be formed in one of positions 2-, 9-, and/or 10- so as to form high molecular weight prodrug compositions. In addition, or alternatively, the compositions of the invention can also include substituted aroyls in position 4-.

For purposes of the present invention, the term "high molecular weight" shall be understood to mean molecular weights of at least about 20,000 Daltons and preferably at least about 30,000 Daltons.

In those aspects of the invention where the taxane is multiply substituted, i.e. more than one of the foregoing positions, it is to be understood that the substituting moieties meed not be the same. Bis-polymeric esters of taxanes are also within the scope of the invention and in some aspects, preferred compounds.

DETAILED DESCRIPTION OF THE INVENTION

A. Introduction

The taxoid-based compositions of the present invention contain one or more substitutions to the native paclitaxel compound. These substitutions enhance water solubility and/or improve therapeutic activity when compared to unmodified paclitaxel or taxane compositions.

B. Taxoids and Taxoid Derivatives

For purposes of the present invention, the term "taxoid" includes all compounds within the taxane family of terpenes and the terms "taxoid" and "taxane" are used interchangeably. Thus, taxol (paclitaxel), 3'-substituted tert-butoxycarbonyl-amine derivatives (taxoteres) and the like as well as other analogs available from, for example, Sigma or other commercial suppliers known to those of ordinary skill in the art are within the scope of the present invention.

Paclitaxel has the following structure:

The substituted taxanes described herein are generally represented by the structure:

Within Formula (I), one of $R_3$, $R_6$, or $R_8$ is

In addition, $R_1$ is selected from the group consisting of aryls, substituted aryls, aralkyls, substituted aralkyls, alkyls and substituted alkyls. $R_2$ is an aryl or substituted aryl. For example, suitable aryls include phenyl and within this aspect, one or both of $R_1$ and $R_2$ are preferably phenyl. Alternative aryls include phenyl, naphthyl, etc. Suitable substituted aryls include 3- and/or 4- halophenyls such as fluorophenyl, chlorophenyl derivatives, 2- or 4-tolyl, 4-methoxyphenyl, 3-dimethylaminophenyl, 4-nitrophenyl, etc. Suitable aralkyls include branched or unbranched $C_{1-8}$ alkyl-containing aryls such as benzyl. Suitable alkyls include branched and unbranched $C_{1-8}$ alkyls, $C_{1-8}$ substituted alkyls.

$R_3$ is H, a $C_{1-10}$ alkoxy, $SiEt_3$, or and

Y is O or S, preferably O;

(n) is zero or a positive integer;

X is oxygen or NL, where L is selected from the group consisting of H, $C_{1-8}$ alkyls, aryls and aralkyls; and

$R_9$ is selected from the group consisting of substantially non-antigenic polymers, $C_{1-12}$ alkyls, $C_{1-12}$ substituted alkyls and bifunctional moieties such as alkyls or polymer containing a terminal group.

In the case of non-antigenic polymers such as PEG derivatives, $R_9$ can be

In certain preferred embodiments, $R_3$ is where (n) is 1 (one), X=O and $R_9$ is a substantially non-antigenic polymer so that prodrug esters are formed.

$R_4$ is H or an aroyl of the formula where Y is O or S and Ar is an aromatic group such as naphthyl, phenyls such as those set forth for $R_{1-2}$, or a substituted aromatic such as meta-azidobenzene. Preferably, $R_4$ is benzoyl or a substituted benzoyl.

In one aspect, $R_5$ and $R_8$ are independently selected from the group consisting of H, $CH_3CO$ and substituted acetic acid derivatives, however, $R_8$ can also be $Si(CH_3)_3$, $Si(C_2H_5)_3$ or where $R_{10}$ is an alkyl, aryl, halogen, or hydrogen and Y is O or S. $CH_3CO$ is preferred for both $R_5$ and $R_8$.

Alternatively, $R_8$ can be and $R_9$ is preferably a polyalkylene oxide.

Within Formula (I), Z is H or $OR_6$ where $R_6$ is selected from the group consisting of H, $C_{1-8}$ alkyls, substituted $C_{1-8}$ alkyls, substituted aryls, aralkyls, substituted aralkyls, $C_{1-10}$ alkoxys, $SiEt_3$,

P is O or OH and is preferably O. It will be understood for purposes of the present invention that the | designation is Formula (I) illustrates that a single or double bond will be found depending upon whether O or OH is selected for P.

As pointed out above, many preferred embodiments of the invention include prodrug-based compositions. The prodrugs are thus chemical derivatives, preferably relatively high molecular weight polymeric derivatives, of the biologically active parent compounds which release the parent compound in vivo from the prodrug carrier. Thus, although (n) can be zero or a positive integer, preferably, (n) is a positive integer and most preferably one (1) so that an ester linkage can be formed which will allow the taxane to be carried into the body as a prodrug and thereafter be liberated as the parent taxane in vivo.

As shown above, $R_9$ is selected from the group consisting of substantially non-antigenic polymers, $C_{1-12}$ alkyls and substituted alkyls. Thus, $R_9$ is a group which enhances at least one of the properties of water solubility and therapeutic activity of the composition when compared to the non-such substituted taxoid or taxane. $R_9$ therefore includes moieties capable of forming simple or preferably polymeric esters. Alternatively, $R_9$ includes moieties capable of forming simple and/or polymeric carbonates. All such moieties can include suitably functionalized, substantially non-antigenic polymers, i.e. mono- or bifunctional PEG, substituted or unsubstituted $C_{1-12}$ alkyls, etc. $R_9$ preferably includes an alkoxy-terminated polyalkylene oxide such as monomethoxy polyethylene glycol, (mPEG). The foregoing thus describes a multitude of taxane-based compositions include taxoid-7-carbonates, 2'-taxoid-PEG-esters and/or simple taxoid-7-carbonates in combination with 2'-PEG esters. Additional esters and/or carbonates are formed when one of $R_3$, $R_6$ and $R_8$ is Substitution of various positions of the taxol molecule have been described. See, for example, Nicolaou, K. et al Angew. Chem Int. Ed. Engl. 1994, 33 15–44 which describes various analogs of taxol, Georg, G. et al. Bioorganic & Medicinal Chem. Let. Vol. 4 No. 19, pp 2331–2336 (1994) which describes substituted 3'-phenyl taxol analogs, and Georg, G. et al. Tetrahedron letters Vol. 15, No 48, pp 8931–8934 (1994) which describes C-4 substituted taxol analogs. In addition, U.S. Pat. Nos. 5,284,865, 5,489,589, 5,278,324, 5,272,171, 4,814,470, 4,942,184, 4,960,790, 5,059,699, 5,227,400, 6,411,984 and 5,530,020 all described various taxanes and substituted taxols which can be further modified in accordance with the present invention. Each of the foregoing publications and patent is incorporated herein by reference. In addition to these specific taxane molecules, the present invention includes taxanes which are modified in those positions as well as in the 2'- and/or 7- positions see, for example, U.S. Pat. No. 5,422,364 which is also incorporated herein by reference. The only limitation on the taxane molecules included herein is that they are capable of undergoing the substitution reactions described herein so that and one of $R_3$, $R_6$ and $R_8$ is One particularly preferred taxane included in the invention is taxotere, available, for example, from Rhone Poulenc Rorer, Collegeville, Pa., having the structure:

This compound can also undergo the modifications in any of the positions described with regard to Formula (II) and $R_1$–$R_8$ herein. For example, as shown in particular detail in Examples 2 and 4, discussing the synthesis of taxotere-2'-PEG ester or diester, the taxotere-containing prodrug compositions of the present invention maintain the $(CH_3)_3CO$ for $R_1$ the Ph for $R_2$ and include the 2'-polymeric ester, as shown below where $R_9$ is mPEG:

Similarly, the bis-taxotere polymeric ester (compound 17, Example 2) can be formed by reacting two equivalents of taxotere with one equivalent of PEG-diacid as shown in Example 2.

Throughout the disclosure, the invention is described with reference to paclitaxel for illustrative purposes. It is to be understood that the modifications described herein are suitable for all taxoids, taxanes and related molecules. The only limitation on this provision is that the selected taxoid must be capable of undergoing at least one of the modifications described herein. Paclitaxel, substituted paclitaxel, taxotere and substituted taxoteres however, are preferred.

C. 2' and 7 Position Substituents

The substituents included in 2'- and/or 7-substituted taxoid-based compositions of the present invention are set forth below as formula (II):

wherein:

(n)=zero or a positive integer;

X=preferably oxygen, although X can also=NL, where L is selected from the group consisting of hydrogen, $C_{1-8}$ alkyls, aryls and aralkyls;

Y is O or S, and

The compositions of the present invention are described as being 2'- and/or 7-position carbonates when (n) is zero or 2' and/or 7 position polymeric esters when (n) is a positive integer. Preferably, (n) is zero or one.

$R_9$ includes substituents such as:

a) substantially non-antigenic polymers which have been suitably functionalized or activated for attachment to the taxoid via the linking portion of (II), which is:

to allow formation of bis-based polymeric prodrugs; or b) $C_{1-12}$ alkyls, $C_{1-12}$ alkylaryls, alkoxy, hydroxy, etc., preferably $C_{1-4}$ alkyls or substituted alkyls. The substituted alkyls can include one or more hydroxy, amino, alkylthio, aryl and aralkyl moieties. These are examples of carbonate substituents.

In the case where 2'-taxane bis-based prodrugs are formed, the 2'-position of each taxane is substituted with the linking moiety (II") shown below:

where $R_9$ is a bifunctional moiety as described above, i.e. PEG.

D. $R_9$ Substantially Non-Antigenic Polymers

In the situations where $R_9$ includes substantially non-antigenic polymers, such as polyalkylene oxides (PAO's), mono-activated, alkyl-terminated PAO's such as monomethoxy-terminated polyethylene glycols (mPEG's) are preferred; bis-activated polyethylene oxides are also contemplated for purposes of loading taxoids or providing a means for attaching other moieties such as targeting agents. For example, the homobifunctional bis succinimidyl carbonate of PEG disclosed in U.S. Pat. No. 5,122,614 or any other alpha, omega homo-substituted polymer can be used. Moreover, hetero-bifunctional polymers are also contemplated.

Although polyethylene glycols vary substantially by weight, polymers having molecular weight ranges of from about 200 to about 80,000 are usually selected for the purposes of the present invention. Molecular weights of from about 1,000 to about 80,000 or from about 20,000 to about 50,000 are preferred and molecular weights ranging from about 30,000 to about 50,000 are particularly preferred.

The polymeric substances included herein are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained. In addition to mPEG, $C_{1-4}$ alkyl-terminated polymers are also useful.

As an alternative to PAO-based polymers, effectively non-antigenic materials such as dextran, polyvinyl pyrrolidones, polyacrylamides, polyvinyl alcohols, carbohydrate-based polymers and the like can be used. Those of ordinary skill and the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immunogenic response in mammals.

In this aspect of the invention, the taxoid-polymer conjugates retain at least a substantial portion of the bioactivity of the taxoid moiety prior to conjugation. For purposes of the present invention, the term "substantial portion of the activity" means that at least some therapeutic effectiveness is maintained. In any event, the advantageous properties of higher aqueous solubility, substantially longer circulating life and reduced antigenicity, either alone or in combination outweigh decrease, if any, of taxoid activity.

E. Carbonate Forming Moieties

When (n) is zero in Formula (I), carbonates are formed in either or both of the 2' and 7 positions of the taxoid. One particularly preferred taxoid includes a 7-methyl carbonate moiety. Other simple 7-position carbonates containing alkyl or aralkyl moieties are possible using $C_{1-12}$ and preferably $C_{1-4}$ alkyl or substituted alkyl groups within the reagents of Formula (IV) which is described in Section G.

F. Synthesis of Substituted Taxoids or Taxanes

The compounds of the present invention are prepared in a manner which takes into account the usually higher reactivity of the 2'-hydroxy group over the other positions of the taxane or taxoid. Thus, if it is not desired to have the 2'-position of the taxane modified, it must be temporarily blocked.

G. 2'-Substituted Taxoids or Taxanes

2'-substituted taxoid derivatives can be prepared by reacting a taxoid or taxane with a reagent having the structure of Formula (III):

$$R_9-X-(CH_2)_n-\overset{\overset{Y}{\|}}{C}-Q \qquad (III)$$

wherein $R_9$, X, Y and (n) are as previously defined and Q is a group capable of being displaced by a nucleophilic reagent. Alternatively, a protecting reagent (IV), as shown below in Section H, can be used. With regard to the Formula (III) reagent, $R_9$ is preferably a polymer having a molecular weight of from about 20,000 to 80,000 as described above in Section D. Q is preferably selected from OH, halides, N-hydroxysuccinimidyl (NHS), N-hydroxybenzotriazolyl, p-nitrophenoxy, imidazolyls and the like. As used herein, Formula (III) is referred to a polymeric ester-forming reagent or a carbonate forming reagent. Activated carbonates or acid chlorides are preferred carbonate forming reagents. Example 1 shows synthesis of a Formula (III) reagent.

When X is NH, the reagents of Formula (IV) can be formed, for example, by first reacting glycine ethyl ester with PEG-acid, followed by saponification, reaction with N-hydroxysuccinimide (NHS) in the presence of dicyclohexylcarbodiimide (DCC).

The 2'-substitution reaction with the compounds of Formula (III) is conducted in the presence of a inert organic solvent such as methylene chloride, toluene, tetrahydrofuran or DMSO, preferably in the presence of a base. The preferred bases include tertiary amines such as triethylamine, diisopropylethylamine, dimethylaminopyridine and pyridine. Pyridine may also serve as a solvent The reaction temperature should be below the decomposition temperature of paclitaxel, preferably from about 4° C. to about 115° C., most preferable from about 25° C. to 60° C. The reaction is preferably conducted with a slight excess of the (Formula III) acylating agent. A general reaction scheme is set forth below in Section H.

H. Protecting Reagents

The non-2'-substituted taxoids are prepared by reacting a starting taxoid derivative, i.e. taxotere or similar substituted taxane with a reagent capable of providing a protective group in the 2'-position. Protective reagents are shown as Formula (IV):

$$R_{11}-X-(CH_2)_m-\overset{\overset{Y}{\|}}{C}-Q \qquad (IV)$$

wherein:
(Q), (X) and (Y) are as defined above,
(m) is a positive integer, preferably one;
$R_{11}$ is a $C_{1-4}$ alkyl, aryls, or other capping group.
Simple acetates, such as $$CH_3-\overset{\overset{}{\|}}{\underset{O}{C}}-$$

can also be used. On preferred protecting moiety is methoxy acetate (MAc). Reaction conditions for attaching the protecting group in the 2' position of the taxoid are the same as those set forth above in Section G. Alternatives to the protective reagents are simply those reagents of Formula (IV). This can be advantageous when the artisan seeks disubstituted taxoids.

The general reaction scheme using reagents (III) or (IV) is set forth below:

A taxane of the formula:

is reacted with a reagent of formula (III) or (IV)

$$R_9-X-(CH_2)_n-\overset{\overset{Y}{\|}}{C}-Q \qquad (III)$$

$$R_{11}-X-(CH_2)_m-\overset{\overset{Y}{\|}}{C}-Q \qquad (IV)$$

whereby a composition of the formula is produced:

where $R_{12}$ is $$R_9-X-(CH_2)_n-\overset{\overset{Y}{\|}}{C}-$$

when (III) is used or $$R_{11}-X-(CH_2)_m-\overset{\overset{Y}{\|}}{C}-$$

if (IV) is used.

I. 7-Substituted Taxoids or Taxanes

Once the 2'-position of the taxoid has been protected or substituted, the 7-carbonate, 7-carbamate or 7-polymeric ester can be formed by reacting a 2'-protected taxoid with a Formula (III) reagent. As was described earlier, when (n) of (III) is zero, a 7-carbonate is formed. When (n) is an integer, a 7-taxane-based ester, such as a polymeric ester, for example, is formed. The reaction conditions, solvents, etc. are the same as those identified above. An illustrative compound, 2'-MAc-7-imidizolyl carbamate is shown below:

The resulting 2' protected taxoid is then reacted with a reagent of Formula (IV) to provide a 7-carbonate group or a 7-PAO ester. If desired, the 2'-protective group can be removed with an equivalent of a nucleophile such as a primary amine such as ethanolamine after the final 7 position modification has been carried out.

The 7-carbonate taxoid derivatives can also be prepared by reacting a 2'-protective taxoid with e.g. phosgene, or derivative thereof such as triphosgene, carbonyl diimidazole or bis succinimidyl carbonate followed by reaction with an alcohol to replace the leaving group (Q) in the 7-position. See FIG. (V) below as an illustration (Q)=chlorine, carbonyl imidazole, succinimidyl carbonate, etc.; $R_1$ is the same as that described above.

This intermediate can be reacted with an alcohol, i.e. ROH, generally, to replace the leaving group (Q). The protecting group in the 2' position can also be removed as described above, if desired.

J. 2',7-Disubstituted Taxoids

Bis-2',7-disubstituted taxoid derivatives i.e. 2',7-diesters, 2',7-carbamates, 2',7-carbonates, can be prepared by reacting a suitable taxoid with about 2 equivalents of a carbonate-forming or ester-forming reagent of Formula (IV) under the conditions set forth in section G. Alternatively, different moieties can be attached by first carrying out the 2' modification with one reagent of Formula (IV) and thereafter with a second Formula (IV) reagent for the 7-position modification.

K. 2-Substituted Taxoids and Taxanes

The invention also includes prodrugs of 2-substituted taxanes. For example, 2-debenzoyl taxol has been reported by Chaudaury et al. in J. Am Chem. Soc. 1994, 116, 4097–4098, the contents of which are incorporated herein by reference. This compound can then be converted into a prodrug by reacting the 2-debenzoyl taxol with a PEG acid in the manner described herein. See Example 3 below. Further 2-substituted taxanes are also contemplated for the present invention. Within Formula (I), $R_4$ is an aroyl of the formula: —C(Y)—Ar, where Ar is an aromatic or substituted aromatic group such as meta-azidobenzene.

L. 4-Substituted Taxoids and Taxanes

Also included herein are prodrugs of 4-substituted taxoids. For example, the 4-deacetyl taxol 6 can be prepared from 4-deacetylbaccatinIII. See, Chen,S-H et al. in J. Org. Chem. 1994, 51, 6156–6158, the contents of which are incorporated herein by reference and Example 4 below for description of the synthesis of a PEG ester. Alternative 4-substituted taxane prodrug compounds can be prepared when $R_5$ is H, $CH_3CO$ or a substituted acetic acid derivative.

M. 9-Substituted Taxoids and Taxanes 9-(R)-substituted taxanes and prodrugs thereof are also within the scope of the present invention. Leping Li et al, J. Med. Chem. 1994, 37, 2665–2663 and Klein L. L., Tetrahedron Lett. 1993, 34, 2047–2050, the contents of each are incorporated herein, describe 9-(R)-dihydro taxol. Briefly stated, the azetidinone side chain is attached to 7-triethylsilyl (TES)-9-(R)-dihydrobaccatin III, in the presence of lithium bis(trimethylsilyl)amide in THF, followed by deprotection of the TES group. See Example 5 below regarding formation of the 9(R)-dihydrotaxol PEG-based prodrug thereof.

N. 10-Substituted Taxoids

The invention also includes prodrugs of 10-substituted taxanes. For example, 10-deacetyl taxol and taxotere have been described. See Chaudaury et al., Tetrahedron Letters 1993, 116, 4921–4924, the contents of which are incorporated herein by reference. Additional 10-substituted taxanes are also contemplated for the present invention. For example, within Formula (I), $R_8$ can also be one of H, $CH_3CO$, or substituted acetic acid derivatives of the formula:

where $R_{10}$ is alkyl, aryl, halogen, hydrogen. Examples 6 and 7 describe formation of prodrugs of 10-substituted taxol and 10-substituted taxotere compounds.

O. Methods of Treatment

Another aspect of the present invention provides methods of treatment for various medical conditions in mammals. The methods include administering an effective amount of a modified taxoid which has been prepared as described herein to the mammal. The compositions are useful for, among other things, treating neoplastic disease, reducing tumor burden, preventing metastasis of neoplasms and preventing recurrences of tumor/neoplastic growths.

The amount of modified taxoid used in the treatment methods is generally described as that amount which effectively achieves the desired therapeutic result in mammals. Naturally, the dosages of the various modified taxoids will vary somewhat depending upon the taxoid moiety and the modifications made at the 2'- and/or 7-position. In general, however, modified taxoid is administered in amounts ranging from about 5 to about 500 mg/m$^2$ per day, based the amount of the taxoid moiety in the conjugate. The range set forth above is illustrative and those skilled in the art will determine the optimal dosing of the conjugate selected based on clinical experience and the treatment indication.

The modified taxoid of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan.

EXAMPLES

Figure 1:
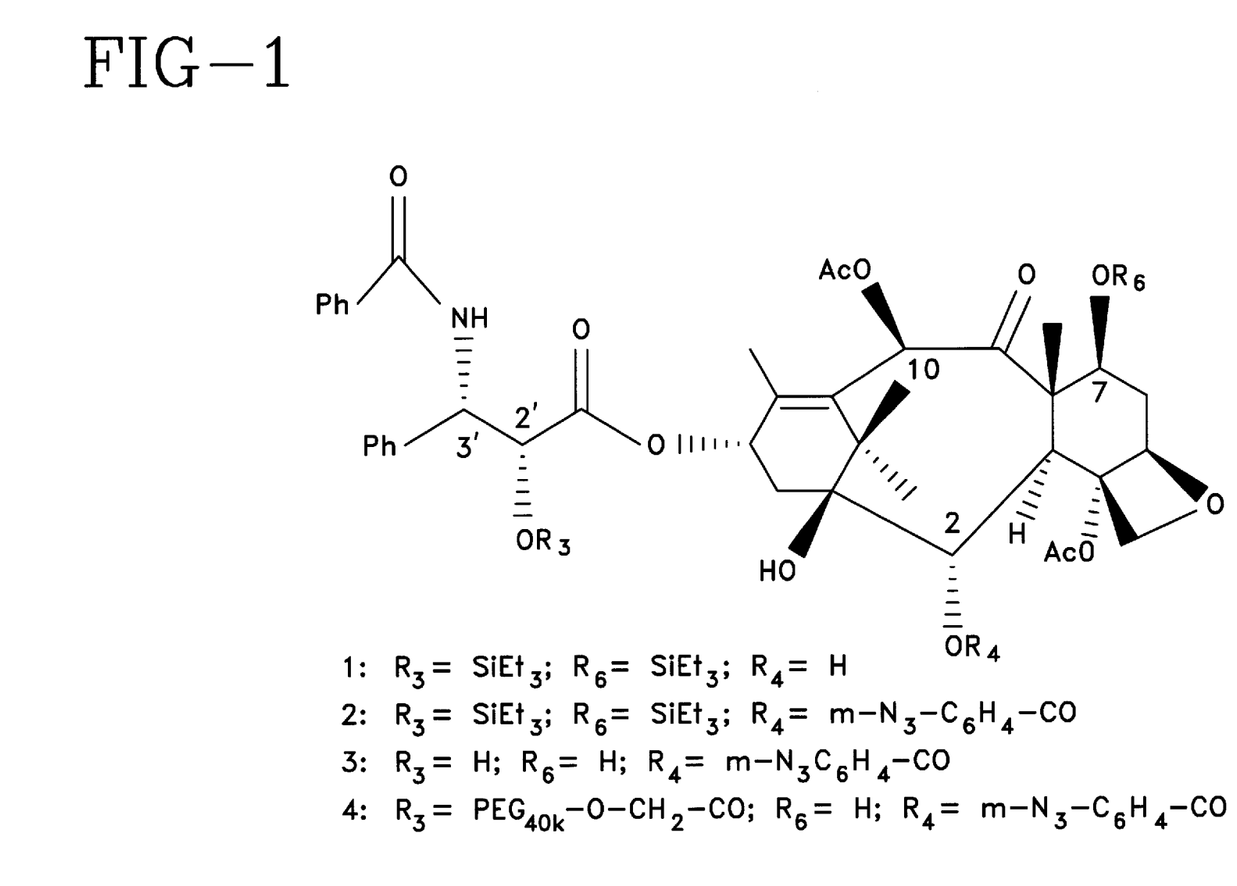
FIGS. 1–5 provide several chemical structures of compounds and intermediates prepared in accordance with the invention.
Figure 2:
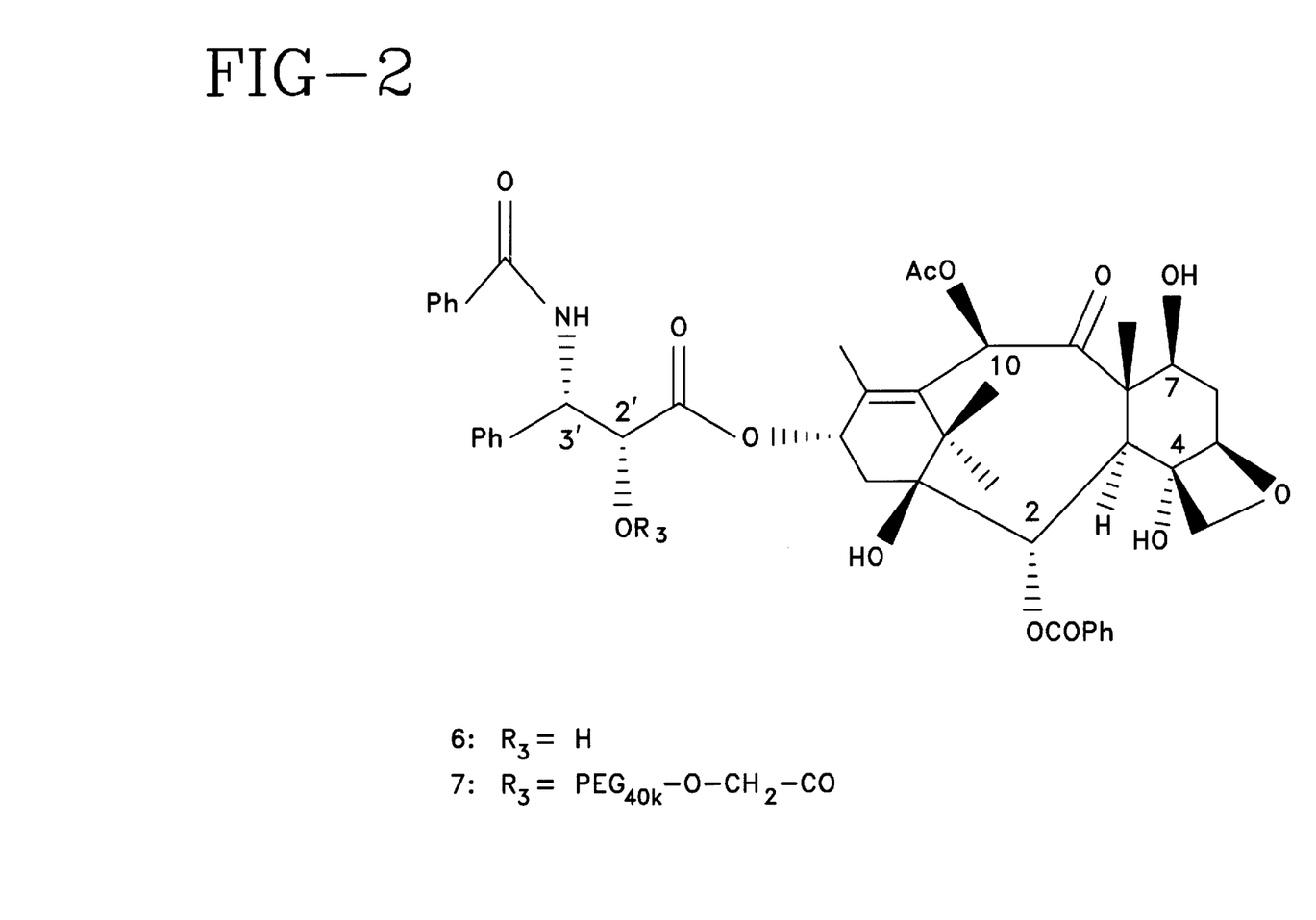
Figure 3:
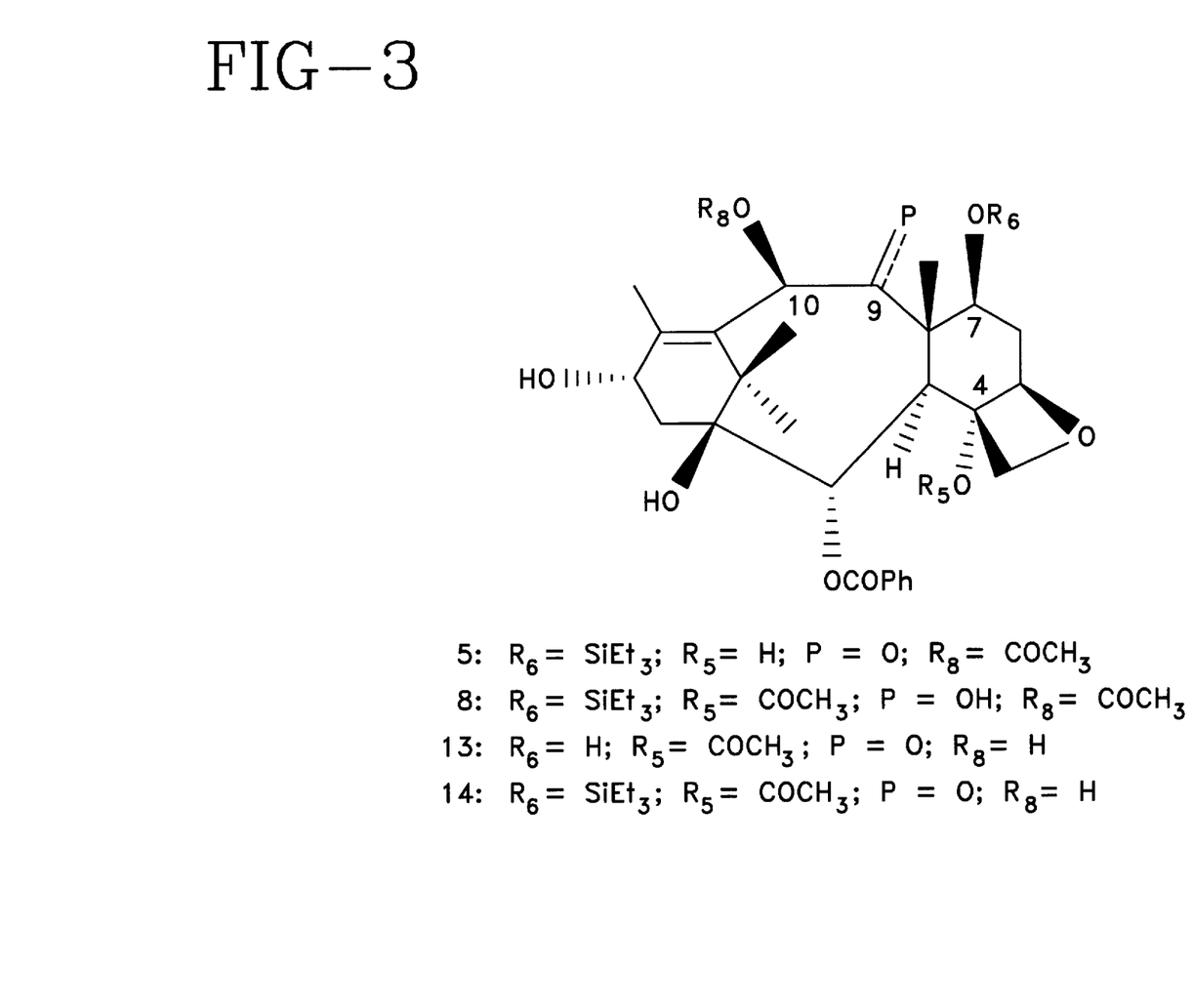
Figure 4:
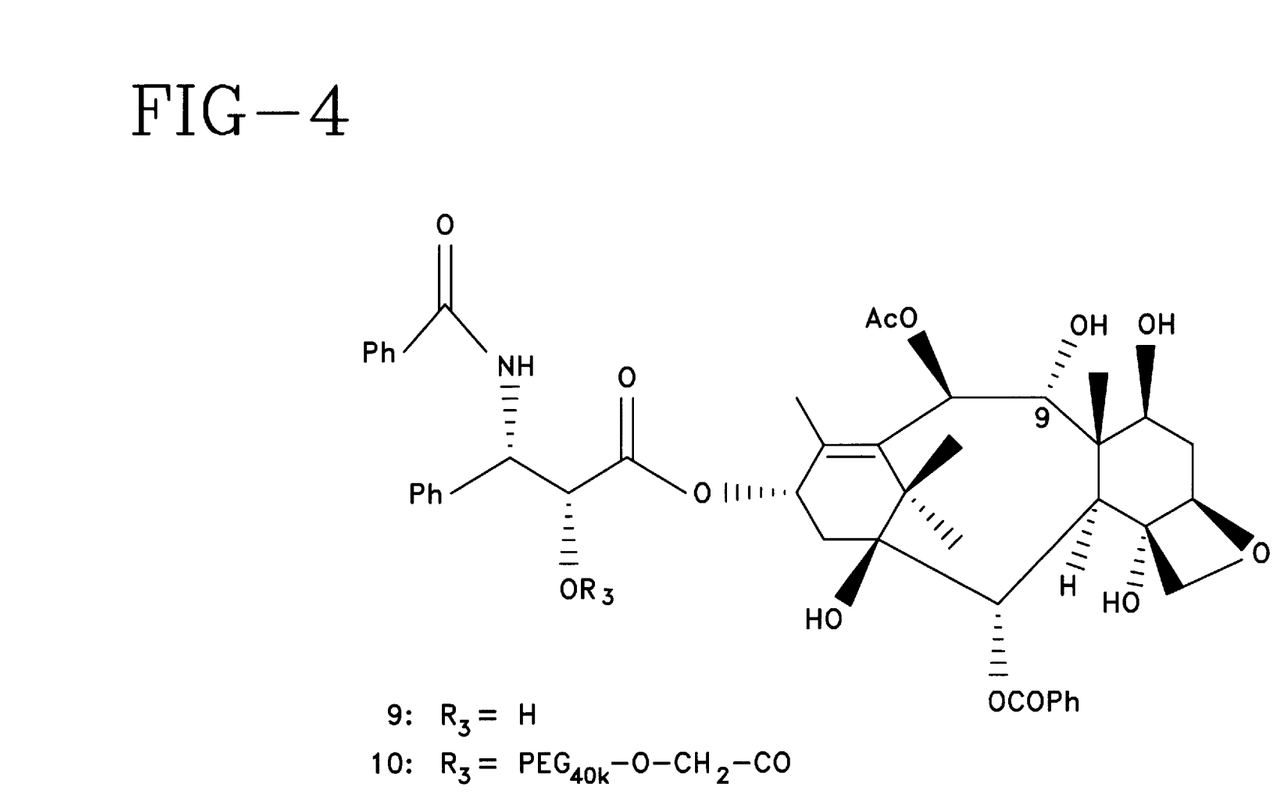
Figure 5:
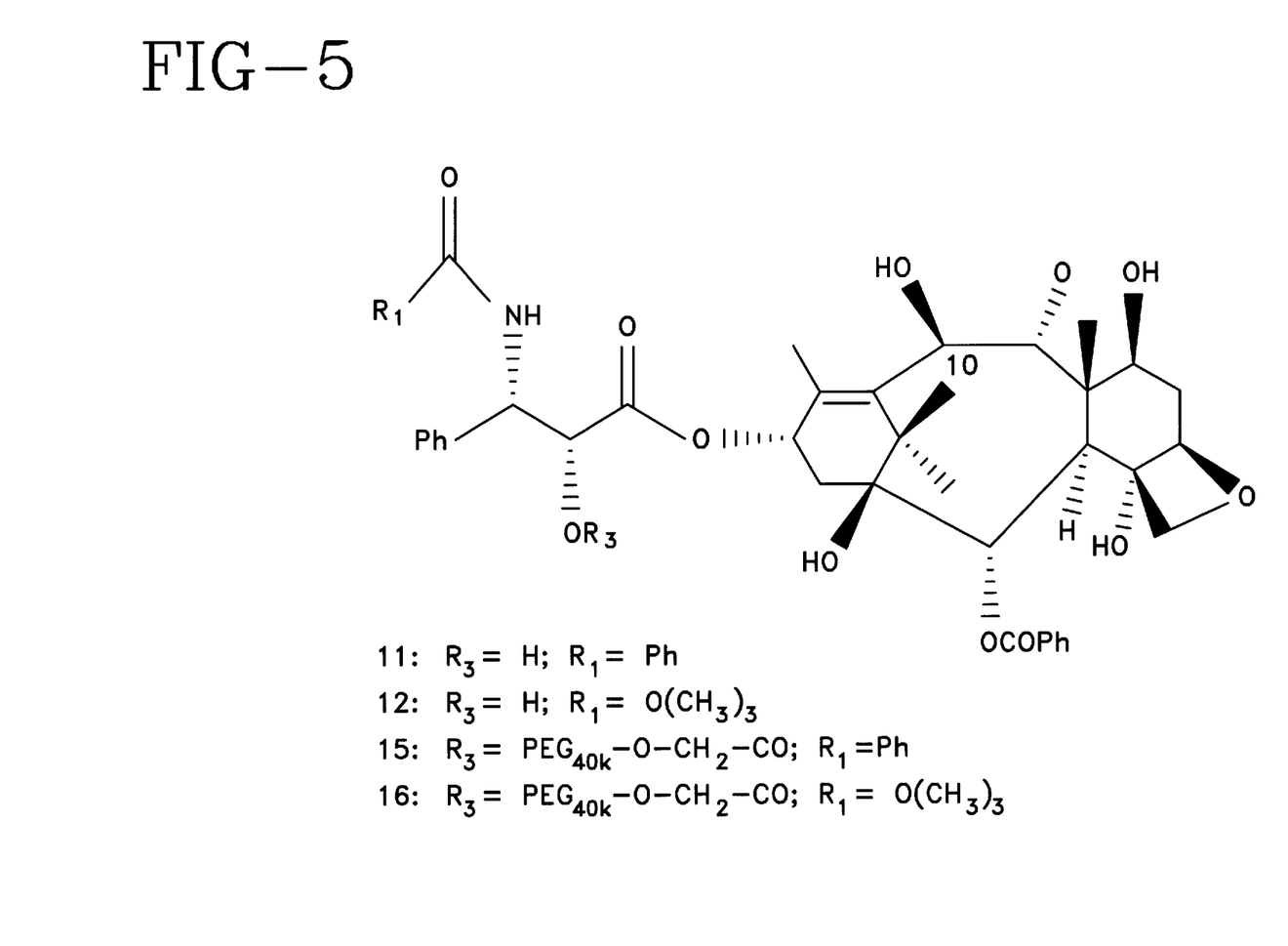

The following examples serve to provide further appreciation of the invention but are not meant in any way to restrict the effective scope of the invention. The compound numbers included in the examples correspond to the numbered compounds set forth in FIGS. 1–5. Abbreviations: TES=Triethylsilyl; PP=Pyrrolidinopyridine; DCC=Dicyclohexyl carbodiimide; DIPC=diisopropylcarbodiimide; DMAP=Dimethylaminopyridine; APTS=Pyridinium p-toluenesulfonate

Example 1

$PEG_{40\ kDa}$ acid(40 g, 1 mmol) was dissolved in methylene chloride (400 mL) and DIPC (32 μl, 0.2 mmol) was added at 0° C. After stirring at this temperature for 30 minutes, N-hydroxysuccinimide (368 mg, 3.2 mmol) was added and the mixture was stirred at room temperature for 3 hours. The solvent was removed and the solid was recrystallized from 2-propanol to give $PEG_{40\ kDa}$-di-N-hydroxy succinimide active ester.

Example 2

Method A:

$PEG_{40\ k}$ester of Taxotere—Compound 17:

$PEG_{40\ kDa}$ diacid (5 g, 0.125 mmol) was dissolved in 20 mL of anhydrous methylene chloride at room temperature and to this solution at 0° C. were added DIPC (52.2 μL, 0.34 mmol), DMAP (64 mg, 0.523 mmol) and taxotere (292 mg, 0.34 mmol) at 0° C. The reaction mixture was allowed to warm to room temperature and left for 16 hours. The solution was washed with 0.1N HCl, dried and evaporated under reduced pressure to yield a white solid which was recrystallized from 2-propanol. The product (80–90% yield) was found to be a mixture of di and monoester.

Method B:

PEG di-N-hydroxy succinimide active ester (2.3 grams, 0.057 mmol) is dissolved in 20 mL of chloroform followed by the addition of taxotere (171 mg, 0.2 mmol) and DMAP (25 mg, 0.2 mmol). The reaction mixture is refluxed for 6 hours. The solution is washed with 0.1N HCl, dried and evaporated under reduced pressure to yield the 2'-PEG diester of taxotere as a white solid.

Example 3

Step A

2',7-bis(triethylsilyl)taxol on treatment with dilute NaOH under phase-transfer conditions gives the 2-debenzoyl product (1). Reacylation of (1) with meta-azido benzoic acid, DCC, PP gives the 2-acyl-2-debenzoyl product(2). Deprotection (HCl/MeOH) provides the final product(3). This procedure allows the synthesis of a 2-acyltaxol analog from taxol in four steps with an unoptimized overall yield of 57%.

Step B

2'-$PEG_{40\ k}$ester of 3—Compound 4:

$PEG_{40\ kDa}$ acid(2.3 grams, 0.057 mmol) is dissolved in 20 mL of anhydrous methylene chloride at room temperature and to this solution at 0° C. are added DIPC (32 μL, 0.2 mmol), DMAP (25 mg, 0.2 mmol) and Compound 3 (199 mg, 0.2 mmol) at 0° C. The reaction mixture is allowed to warm to room temperature and left for 16 hours. The solution is washed with 0.1N HCl, dried and evaporated under reduced pressure to yield 4 as a white solid.

Example 4

Step A:

4-deacetyl taxol 6 was prepared from 4-deacetylbaccatin III according to the method of Chen,S-H et al(JOC 1994, 51,6156–6158). 7-TES-bacattin III on reduction with superhydride (LiBHEt₃,THF) according to the above reference (Chen et al) gives 7-TES-4-deacetylbaccatin 5. The side chain is then attached to 5, using DCC, DMAP, similar to the procedure of Example 3, followed by deprotection of the TES group with APTS, MeOH at room temperature to give 4-deacetyl taxol 6.

Step B:

$PEG_{40\ k}$ester of 6—Compound 7:

$PEG_{40\ kDa}$ acid(2.3 grams, 0.057 mmol) is dissolved in 20 mL of anhydrous methylene chloride at room temperature and to this solution at 0° C. are added DIPC (32 μL, 0.2 mmol), DMAP (25 mg, 0.2 mmol) and Compound 6 (199 mg, 0.2 mmol) at 0° C. The reaction mixture is allowed to warm to room temperature and left for 16 hours. The solution is washed with 0.1N HCl, dried and evaporated under reduced pressure to yield 7 as a white solid.

Example 5

Step A:

9(R) dihydro taxol 9 was prepared from 7-TES-9-(R)-dihydro-baccatin III 8 according to the method of Leping Li et al (J. Med. Chem. 1994, 37, 2655–2663) and by the method of Klein L. L (Tetrahedron Lett. 1993, 34 2047–2050). The azetidinone side chain is attached to 7-TES-9(R)-dihydro-baccatin III, 8 in presence of lithium bis(trimethylsilyl)-amide in THF, followed by deprotection of TES group with 1% HCl in ethanol at 0° C. to give 9(R) dihydro taxol 9.

Step B:

$PEG_{40\ k}$ester of 9—Compound 10:

$PEG_{40\ kDa}$ acid (2.3 grams, 0.057 mmol) is dissolved in 20 mL of anhydrous methylene chloride at room temperature and to this solution at 0° C. are added DIPC (32 μL, 0.2 mmol), DMAP (25 mg, 0.2 mmol) and Compound 9 (171 mg, 0.2 mmol) at 0° C. The reaction mixture is allowed to warm to room temperature and left for 16 hours. The solution is washed with 0.1N HCl, dried and evaporated under reduced pressure to yield 10 as a white solid.

Example 6

Step A:

10-deacetyl taxol 11 and taxotere 12 are prepared from 10-deacetylbaccatin III 13 according to the method of Chaudaury et al (Tetrahedron. Lett.1993, 116, 4921–4924.) 7-TES-10-deacetyl-baccatin III 14 is coupled with the protected taxol or taxotere side chain by the use of DCC and 4-pyrrolidinopyridine (PP), followed by deprotection with HCOOH at 25° C. to give the 10-deacetyl taxol 15 and taxotere 16.

Step B:

$PEG_{40\ k}$ester of 11—Compound 15:

$PEG_{40\ kDa}$ acid (2.3 grams, 0.057 mmol) is dissolved in 20 mL of anhydrous methylene chloride at room temperature and to this solution at 0° C. are added DIPC (32 μL, 0.2 mmol), DMAP (25 mg, 0.2 mmol) and Compound 11 (199 mg, 0.2 mmol) at 0° C. The reaction mixture is allowed to warm to room temperature and left for 16 hrs. The solution is washed with 0.1N HCl, dried and evaporated under reduced pressure to yield 15 as a white solid.

Example 7

$mPEG_{40\ k}$ester of Taxotere:

$mPEG_{40\ k}$ acid (2.3 grams, 0.057 mmol) is dissolved in 20 mL of anhydrous methylene chloride at room temperature and to this solution at 0° C. are added DIPC (32 μL, 0.2 mmol), DMAP (25 mg, 0.2 mmol) and Compound 12 (199 mg, 0.2 mmol) at 0° C. The reaction mixture is allowed to warm to room temperature and left for 16 hrs. The solution is washed with 0.1N HCl, dried and evaporated under reduced pressure to yield title compound as a white solid.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention. Numerous references are cited in the specification, the disclosures of which are incorporated by reference in their entireties.

We claim:

1. A taxane-based composition comprising a moiety of the formula:

wherein:

$R^1$ is selected from the group consisting of aryls, substituted aryls, aralkyls, substituted aralkyls, alkyls and substituted alkyls;

$R^2$ is an aryl or substituted aryl;

$R^3$ is H, a $C_{1-10}$ alkoxy, SiEt$_3$, or

Y is O or S;

$R^4$ is H or an aroyl of the formula where Ar is an aromatic, substituted aromatic or heteroaromatic group;

$R^5$ is H, CH$_3$CO or a substituted acetic acid derivative;

Z is H or OR$_6$ where R$_6$ is selected from the group consisting of H, $C_{1-8}$ alkyls, $C_{1-8}$ substituted alkyls, $C_{1-8}$ alkoxy, $C_{1-8}$ aralkyls, substituted aryls, aralkyls, substituted aralkyls, SiEt$_3$, P is O or OH;

(n) is zero or a positive integer;

X is oxygen or NL, where L is selected from the group consisting of hydrogen, $C_{1-8}$ alkyls, aryls and aralkyls; and

$R_8$ is H, Si(CH$_3$)$_3$, Si(C$_2$H$_5$)$_3$, CH$_3$CO, or a substituted acetic acid derivative of the formula:

where $R_{10}$ is an alkyl, aryl, halogen or hydrogen, or

$R_9$ is selected from the group consisting of substantially non-antigenic polymers substituted $C_{1-12}$ alkyls, $C_{1-12}$ alkyls, and bifunctional moieties containing a terminal group of the formula:

and one of $R_3$, $R_6$ and $R_8$ is

2. The composition of claim 1, wherein $R_1$ is (CH$_3$)$_3$CO, $R_2$ is phenyl and $R_3$ is 3. The composition of claim 1, wherein X is oxygen.

4. The composition of claim 1, wherein (n) is 1.

5. The composition of claim 1, wherein $R_4$ is phenyl.

6. The composition of claim 1, wherein said $R_9$ substituted alkyls comprise a member of the group consisting of hydroxy, amino, alkylthio, aryl and aralkyl moieties.

7. The composition of claim 1, wherein said substantially non-antigenic polymer is a polyalkylene oxide.

8. The composition of claim 7, wherein said polyalkylene oxide comprises an alkyl terminal.

9. The composition of claim 8, wherein said alkyl-terminated polyalkylene oxide is a monomethoxy-terminated polyethylene glycol, (mPEG).

10. The composition of claim 1, wherein said substantially non-antigenic polymer has a molecular weight of from about 200 to about 80,000.

11. The composition of claim 10, wherein said substantially non-antigenic polymer has a molecular weight of from about 1,000 to about 80,000.

12. The composition of claim 11, wherein said substantially non-antigenic polymer has a molecular weight of from about 20,000 to about 50,000.

13. The composition of claim 1, wherein $R_3$ is

14. The composition of claim 1, wherein $R_5$ is CH$_3$CO.

15. The composition of claim 1, wherein Z is OR$_6$ and R$_6$ is

16. The composition of claim 1, wherein $R_8$ is

17. The composition of claim 1, wherein said polymer is selected form the group consisting of dextran, polyvinyl pyrrolidones, polyacryl amides, polyvinyl alcohols and carbohydrate-based polymers.

18. The composition of claim 1, wherein P is O.

19. The composition of claim 1, wherein P is OH.

20. The composition of claim 13, wherein $R_9$ is a homo-bifunctional polyalkylene oxide, the alpha terminal thereof linked to X.

21. The composition of claim 20, wherein the omega terminal of said polyalkylene oxide is linked to a taxane.

22. A method of treating a condition selected from the group consisting of neoplastic disease, tumor burden, neoplastic metastasis, recurrences of tumor growth and recurrences of neoplastic growth in mammals, comprising administering an effective amount of a taxane composition of claim 1.

23. A method of preparing a taxane-based composition, comprising reacting a taxane of the formula:

wherein:

$R_1$ is selected from the group consisting of aryls, substituted aryls, aralkyls, substituted aralkyls, alkyls and substituted alkyls;

$R_2$ is an aryl or substituted aryl;

$R_4$ is H or an aroyl of the formula where Ar is an aromatic, substituted aromatic or heteroaromatic group;

$R_5$ is H, $CH_3CO$ or a substituted acetic acid derivative;

Z is H or $OR_6$ where $R_6$ is selected from the group consisting of H, $C_{1-8}$ alkyls, $C_{1-8}$ substituted alkyls, $C_{1-8}$ alkoxy, $C_{1-8}$ aralkyls, substituted aryls, aralkyls, substituted aralkyls, $SiEt_3$,

P is O or OH;

(n) is zero or a positive integer;

X is oxygen or NL, where L is selected from the group consisting of hydrogen, $C_{1-8}$ alkyls, aryls and aralkyls;

Y is O or S;

$R_8$ is H, $Si(CH_3)_3$, $Si(C_2H_5)_3$, $CH_3CO$, or a substituted acetic acid derivative of the formula:

where $R_{10}$ is an alkyl, aryl, halogen or hydrogen, or

$R_9$ is selected from the group consisting of substantially non-antigenic polymers, substituted $C_{1-12}$ alkyls, $C_{1-12}$ alkyls, and bifunctional moieties containing a terminal group of the formula:

with a reagent selected from the group consisting of and wherein:

(n), X, Y, and $R_9$ are as set forth above;

(m) is a positive integer;

$R_{11}$ is a $C_{1-4}$ alkyl, aryls, or other capping group; and

Q is a group capable of being displaced by a nucleophilic reagent and is selected from the group consisting of OH, halides, N-hydroxysuccinimidyl, N-hydroxybenzotriazolyl, p-nitrophenoxy and imidazolyls;

whereby a composition is produced of the formula where $R_{12}$ is when (III) is used and when (IV) is used.

24. The method of claim 23, wherein X is oxygen.
25. The method of claim 23, wherein (n) is 1.
26. The method of claim 23, wherein said substantially non-antigenic polymer is a polyalkylene oxide.
27. The method of claim 23, wherein said substantially non-antigenic polymer has a molecular weight of from about 20,000 to about 80,000.
28. The method of claim 27, wherein said substantially non-antigenic polymer has a molecular weight of from about 30,000 to about 50,000.

* * * * *

UNITED STATES PATENT AND TRADEMARK OFFICE
CERTIFICATE OF CORRECTION

PATENT NO. : 5,824,701

Page 1 of 3

DATED : October 20, 1998

INVENTOR(S) : GREENWALD, et al.

It is certified that error appears in the above-identified patent and that said Letters Patent is hereby corrected as shown below:

Column 1, line 45: "non-queous" should read --non-aqueous--;
Column 2, line 39: "$C_{1-10}$alkoxys" should read --$C_{1-10}$ alkoxyls--;
Column 3, line 38: "muitiply" should read --multiple--;
Column 3, line 40: "meed" should read --need--;
Column 5, line 45: "and" should read --any--;
Column 9, line 63: "On" should read --One--;
Column 10, line 67: 2'-MAc-7-imidizolyl" should read --2'MAc-7-imidazolyl--;

Column 11, lines 1-13 should read

--;

UNITED STATES PATENT AND TRADEMARK OFFICE
CERTIFICATE OF CORRECTION

PATENT NO. : 5,824,701

DATED : October 20, 1998

INVENTOR(S) : GREENWALD, et al.

It is certified that error appears in the above-identified patent and that said Letters Patent is hereby corrected as shown below:

Column 11, lines 27-38:  "  "

should read

—  —;

UNITED STATES PATENT AND TRADEMARK OFFICE
CERTIFICATE OF CORRECTION

PATENT NO. : 5,824,701
DATED : October 20, 1998
INVENTOR(S) : GREENWALD, et al.

It is certified that error appears in the above-identified patent and that said Letters Patent is hereby corrected as shown below:

Column 13, lines 10 and 23: "is" should read --was--;
Column 14, line 17: "is" should read --was--;
Claim 1, line 18 (Column 15, line 29): "$R^1$" should read --$R_1$--;
Claim 1, line 21 (Column 15, line 32): "$R^2$" should read --$R_2$--;
Claim 1, line 22 (Column 15, line 33): "$R^3$" should read --$R_3$--;
Claim 1, line 29 (Column 15, line 40): "$R^4$" should read --$R_4$--;
Claim 1, line 38 (Column 15, line 49): "$R^5$" should read --$R_5$--;
Claim 1, line 63 (Column 16, line 13): "polymers substituted" --polymer, substitued--; and
Claim 17, line 2 (Column 17, line 12): "form" should read --from--.

Signed and Sealed this

Sixth Day of April, 1999

Q. TODD DICKINSON

*Attest:*

*Attesting Officer*   Acting Commissioner of Patents and Trademarks